(12) United States Patent
Hu et al.

(10) Patent No.: US 12,336,962 B2
(45) Date of Patent: Jun. 24, 2025

(54) STERILE PREPARATION, SUBPACKAGE AND OUTPUT SYSTEM FOR SERUM AND METHOD THEREFOR

(71) Applicant: HENAN FANGZHOU MEDICAL INSTRUMENT CO., LTD., Henan (CN)

(72) Inventors: Zhichao Hu, Henan (CN); Xiaojing Zheng, Henan (CN); Hui Wang, Henan (CN); Lichao Shen, Henan (CN)

(73) Assignee: HENAN FANGZHOU MEDICAL INSTRUMENT CO., LTD., Henan (CN)

( * ) Notice: Subject to any disclaimer, the term of this patent is extended or adjusted under 35 U.S.C. 154(b) by 517 days.

(21) Appl. No.: 17/916,423

(22) PCT Filed: Jul. 13, 2021

(86) PCT No.: PCT/CN2021/106106
§ 371 (c)(1),
(2) Date: Sep. 30, 2022

(87) PCT Pub. No.: WO2022/028219
PCT Pub. Date: Feb. 10, 2022

(65) Prior Publication Data
US 2023/0149261 A1 May 18, 2023

(30) Foreign Application Priority Data
Aug. 1, 2020 (CN) .......................... 202010764034.3

(51) Int. Cl.
*A61J 1/14* (2023.01)
*A61J 1/20* (2006.01)
*A61M 1/36* (2006.01)

(52) U.S. Cl.
CPC ........... *A61J 1/1456* (2015.05); *A61J 1/1418* (2015.05); *A61J 1/2058* (2015.05); *A61J 1/2096* (2013.01);
(Continued)

(58) Field of Classification Search
CPC ...... A61J 1/1456; A61J 1/1418; A61J 1/2058; A61J 1/2096; A61M 1/3693; A61M 2202/0413; G01N 33/491; B01L 3/5021
See application file for complete search history.

(56) References Cited

U.S. PATENT DOCUMENTS

| 3,983,037 A | 9/1976 | Lee et al. |
| 2019/0240394 A1* | 8/2019 | Horvath ..................... A61L 2/08 |
| 2021/0244870 A1* | 8/2021 | Oronsky ............... A61M 1/342 |

FOREIGN PATENT DOCUMENTS

| CN | 1713944 A | 12/2005 |
| CN | 201058029 Y | 5/2008 |

(Continued)

OTHER PUBLICATIONS

International Search Report issued in application WO 2022028219 A1, mailed Sep. 24, 2021.

*Primary Examiner* — Kaylee R Wilson
*Assistant Examiner* — Rachel O'Connell
(74) *Attorney, Agent, or Firm* — McClure, Qualey & Rodack, LLP

(57) ABSTRACT

The present disclosure belongs to a sterile preparation, subpackage and output system for serum and a method therefor. The system includes a blood collection and separation unit configured to collect venous blood and capable of achieving centrifugal separation of blood; a serum collection unit cooperating with the blood collection and separation unit and configured to achieve sterile collection of serum; a liquid subpackage unit cooperating with the serum collection unit and configured to achieve precise sterile subpack- (Continued)

age of the serum; and a liquid boosting pen configured to achieve precise quantitative output of the serum. The system has the characteristics that the structure is simple, the overall process is simple and controllable, the safe and long-term storage of the serum is guaranteed, the waste of the serum and the blood drawing capacity are reduced, and the burden and negative emotion of a patient are relieved.

12 Claims, 9 Drawing Sheets

(52) U.S. Cl.
CPC ... *A61M 1/3693* (2013.01); *A61M 2202/0413* (2013.01)

(56) References Cited

FOREIGN PATENT DOCUMENTS

| | | | |
|---|---|---|---|
| CN | 201469752 U | * | 5/2010 |
| CN | 208693799 U | | 4/2019 |
| CN | 111265224 A | | 6/2020 |
| CN | 111728867 A | | 10/2020 |
| CN | 212261884 U | | 1/2021 |

* cited by examiner

STERILE PREPARATION, SUBPACKAGE AND OUTPUT SYSTEM FOR SERUM AND METHOD THEREFOR

FIELD

The present disclosure belongs to the technical field of blood products, in particular relates to a sterile preparation, subpackage and output system for serum and a method therefor.

BACKGROUND

Various growth factors, vitamins, proteins and the like enriched in the serum of human bodies are approximately identical to components of tear and are similar to natural tear in biological characteristics, and therefore, the serum may be used as a tear substitute, may also provide a good environment for the ocular surface and play a role in repairing the ocular surface, and may be used for treatment of ocular surface diseases and tissue repair after surgical reconstruction. In past 15 years, a large number of research papers have been published, the treated indications mainly including dry eye disease (DED), persistent epithelial defect (PED), ocular graft versus host disease (oGVHD), recurrent corneal erosion (RCE), neurotrophic keratitis (NK) and limbal stem cell deficiency (LSTD) have been continuously increased. There are also some documents which suggest that autoserum is externally used for ear-dripping therapy and ear perforation, and standardized application of the autoserum has been performed in many countries such as America, Australia and the United kingdom.

Known by collecting documentations, a preparation process of domestic autoserum eye drops includes: on an empty stomach, collecting 5 ml of ulnar venous blood in a sterile centrifugal tube, keeping standing at normal temperature for 1-2 h, performing centrifugation at the rotating speed of 3500 r/min for 10 min, extracting serum on the upper layer in the centrifugal tube by using a 5 ml disposable sterile syringe, subpackaging the serum into two empty sterile eye drop bottles, storing the bottles into a 4° C. refrigerator for later use, and meanwhile, marking out the bed number, name and autoserum preparation time of a patient. The above-mentioned process is a method frequently used in clinic in China. Although the method is convenient and easy to obtain, no sterility safeguard measures are provided, and meanwhile, the amount of the prepared serum does not conform to the use course of treatment of the autoserum. After two or three days since the serum is used up, a patient still needs to endure the pain caused by drawing blood to repeatedly queue up for drawing blood on an empty stomach, and a patient who is not hospitalized needs to go to hospital and go back repeatedly; and no standardized product has been formed at present. There are the following defects in the above-mentioned operation process: 1, the operation is not sterile operation and is not performed in a sterile laboratory so as not to conform to the standard of large-scale promotion and application; 2, the serum is simple in storage and package so as not to meet the demand on long-term use or is complex in package so as to be inconvenient to use and increase the use cost; 3, the serum needs to be put into cold storage and even frozen in a storage process, and the volume of the serum is increased in the freezing process so that the package is easily damaged; 4, precise serum subpackage cannot be achieved, which causes excessive serum in one part of storage package and insufficient serum in the other part of storage package, and therefore, the serum is not only inconvenient to store, but also inconvenient to precisely and quantitatively use later; and 5, the serum cannot be precisely and quantitatively output, and therefore, the situation that a great deal of serum is wasted occurs in the use process.

SUMMARY

The present disclosure aims at overcoming defects in the prior art to provide a sterile preparation, subpackage and output system for serum and a method therefor, by which a closed-loop preparation and extraction process is adopted, so that direct contact between a sample and air is reduced, the risk of contamination is reduced, and autoserum which can be stored for a long term is prepared; due to the sterility design of the system, equipment investments of a medical institution are reduced, and the preparation and use costs are reduced; a standard operation process is provided by devices, so that the preparation time is shortened; and meanwhile, precise sterile subpackage and precise quantitative liquid output can be achieved, the safe storage of the serum is guaranteed, the waste of the serum and the blood drawing capacity are reduced, and the burden and negative emotion of a patient are relieved.

In order to achieve the above-mentioned objectives, the present disclosure adopts the technical solutions.

Provided is a sterile preparation, subpackage and output system for serum, wherein the system includes: a blood collection and separation unit configured to collect venous blood and capable of achieving centrifugal separation of the blood; a serum collection unit cooperating with the blood collection and separation unit and configured to achieve sterile collection of serum; a liquid subpackage unit cooperating with the serum collection unit and configured to achieve precise sterile subpackage of the serum; and a liquid boosting pen configured to achieve precise quantitative liquid output of the serum.

Preferably, the blood collection and separation unit includes a container main body, wherein an inner cavity of the container main body is provided with a first piston matched with the inner cavity, a detachable push rod is disposed on the outer side of the first piston, a venous blood collection opening in the bottom of the container main body is provided with a first Luer taper, and the first Luer taper is provided with a blood collection needle or an end cap matched with the first Luer taper; and a skirt part on the top end of the first piston is provided with a notch, and the tail end of the push rod is matched with the notch.

Preferably, the serum collection unit includes a syringe and a needle seat used for supporting an injection needle, wherein the front end of the syringe is connected to the injection needle by a medical tee; the needle seat is of an inverted funnel-shaped cavity structure of which the upper and lower bottom surfaces communicate; and a third end of the medical tee is connected to the liquid subpackage unit.

Preferably, the liquid subpackage unit includes several subpackage bottles that are connected in series; the subpackage bottle located on the front end is connected to the third end of the medical tee by a second Luer taper, and the subpackage bottle located on the tail end is provided with a first connection hose with a 0.2 μm-pore-size bacteriostatic filter.

Preferably, the subpackage bottle includes a bottle body, wherein the front end of the bottle body is provided with a bottle cap, a rear cover is screwed to the tail end of the bottle body, a second piston is disposed inside the bottle body, and a first spring is disposed between the second piston and the rear cover; a gland is screwed to the outer side of the rear cover, the rear cover and the gland are each provided with a hole, and a filtration membrane is disposed between the rear cover and the gland.

Preferably, graduation lines are disposed between the front end and the tail end of the bottle body, and the part, corresponding to the tail ends of the graduation lines, of the bottle body is provided with a connecting end; the bottle cap of the subpackage bottle located on the front end is connected to the second Luer taper by a second connection hose; in two adjacent subpackage bottles, the connecting end of the front subpackage bottle is connected to the bottle cap of the rear subpackage bottle by a third connection hose; and the connecting end of the subpackage bottle located on the tail end is provided with the first connection hose with the 0.2 μm-pore-size bacteriostatic filter.

Preferably, the liquid boosting pen includes a pen cap and a pen body supporting tube screwed to the tail end of the pen cap, and an adjustable rear cover is screwed to the tail end of the pen body supporting tube; the bottle body of the subpackage bottle and the second piston disposed inside the bottle body are disposed inside the pen cap and the pen body supporting tube, the second piston is connected to a push rod disposed inside a ratchet tube, continuous ratchet teeth are disposed on the outer circumferential surface of the ratchet tube, a push rod positioning frame and a boosting frame are disposed inside the pen body supporting tube, the top of the boosting frame is connected to a button, a second spring is disposed between the button and the pen body supporting tube, and the top end of the button penetrates through the adjustable rear cover; the push rod positioning frame includes a first mounting rack that is snap-fitted in the pen body supporting tube, and positioning push rods disposed at the bottom of the first mounting rack and matched with the continuous ratchet teeth; the boosting frame is disposed on the inner side of the push rod positioning frame and includes boosting push rods matched with the continuous ratchet teeth, and a second mounting rack is disposed on the tops of the boosting push rods; and the front end of the bottle body penetrates through the top of the pen cap.

Preferably, the continuous ratchet teeth are disposed on the two corresponding sides of the outer circumferential surface of the ratchet tube, the push rod positioning frame includes the two positioning push rods respectively matched with the continuous ratchet teeth located on the two sides, and the boosting frame includes the two boosting push rods respectively matched with the continuous ratchet teeth located on the two sides; a groove is disposed at the bottom end of the button, and the second mounting rack is snap-fitted in the groove; and a ratchet tube notch is disposed on one side of the lower parts of the continuous ratchet teeth.

The present disclosure further provides a method for a sterile preparation, subpackage and output system for serum, and the method includes the following steps:

step 1: connecting a push rod to a first piston, enabling a blood collection needle to be fixedly connected to a first Luer taper, and after the connection is completed, collecting venous blood;

step 2: after the collection of the venous blood is completed, dismounting the blood collection needle from the first Luer taper, and mounting an end cap; and dismounting the push rod from the first piston;

step 3: after the push rod and the blood collection needle are dismounted and the end cap is mounted, incubating and centrifuging whole blood in a container main body, and layering centrifuged erythrocytes and serum, wherein the serum is a supernate;

step 4: placing a needle seat which is of an inverted funnel-shaped cavity structure at the outer side of the first piston, and enabling an injection needle to penetrate through the upper bottom surface of the needle seat, the lower bottom surface of the needle seat and the first piston to enter the serum serving as the supernate;

step 5: adjusting a medical tee to enable a cavity of a syringe to communicate with the container main body, and pressing a barrel of the syringe to enable the serum serving as the supernate to enter the cavity of the syringe via the container main body, the injection needle and the medical tee;

step 6: adjusting the medical tee to enable the cavity of the syringe to communicate with a liquid subpackage unit, and boosting a pull rod of the syringe 9 to enable the serum inside the cavity of the syringe to enter the liquid subpackage unit via the medical tee;

step 7: after enabling the serum inside the cavity of the syringe to enter the liquid subpackage unit in step 6 is completed, completing subpackage; and after the subpackage is completed, disassembling the liquid subpackage unit into several subpackage bottles, and performing storage in a low-temperature or freezing manner;

step 8: when the serum needs to be used, enabling positioning push rods and boosting push rods to be matched with ratchet teeth located on the same position on a ratchet tube; putting a bottle body into a pen cap, and connecting a push rod inside the ratchet tube to a second piston in the bottle body; and meanwhile, screwing the pen cap to a pen body supporting tube, mounting a second spring and a button, and finally, screwing an adjustable rear cover to the pen body supporting tube;

step 9: placing the bottle body on the top of the pen cap above a position where the serum needs to be dripped, manually pressing the button, driving, by the button, a boosting frame to move towards the pen cap end, pushing, by the top ends of the boosting push rods, the ratchet tube 32 to advance via the ratchet teeth, and pushing, by the push rod in the ratchet tube, the second piston to move towards the front end of the bottle body to quantitatively output the serum;

step 10: when the above-mentioned boosting push rods push the ratchet tube to advance, keeping the positions of the positioning push rods unchanged, and enabling the top ends of the positioning push rods to enter the next ratchet teeth of continuous ratchet teeth; after the quantitative output of the serum is completed, releasing the button to enable the button to be restored under the action of the second spring, keeping the positions of the positioning push rods for fixing the ratchet tube unchanged in a restoring process, and enabling the boosting push rods to be restored under the driving of the button and enter the same ratchet teeth which the top ends of the positioning push rods enter, thus completing the overall process of quantitative output of the serum;

step 11: after the serum in one subpackage bottle is used up, replacing the subpackage bottle with a new subpackage bottle, wherein top ends of the positioning push rods and the boosting push rods may enter the continuous ratchet teeth via ratchet tube notches during replacement; and step 12: disposing an external thread on the outer circumferential surface of the tail end of the pen body supporting tube, connecting the external thread on the tail end of the pen body supporting tube to an internal thread of the adjustable rear cover, and adjusting the stroke of the second spring by adjusting the distance between the pen body supporting tube and the adjustable rear cover; wherein the shorter the stroke of the second spring, the smaller the amount of the serum output every time, and the longer the stroke of the second spring, the greater the amount of the serum output every time.

Preferably, the specific process of enabling the serum inside the cavity of the syringe to enter the liquid subpackage unit via the medical tee in the step 6 is that: the pull rod of the syringe is boosted to enable the serum inside the syringe to enter the subpackage bottle located on the front end, the pressure inside the subpackage bottle is increased, the second piston is pushed to move towards a gland side while the pressure is increased, and when the second piston moves to a first spring, a connecting end is opened; after the connecting end is opened, the serum inside the syringe continuously enters the subpackage bottle located on the front end, and the second piston causes the connecting end to be completely opened under the pressure of the serum and the serum enters the next subpackage bottle; and after filling of all the serum inside the syringe is completed, the subpackage process is ended;

in the above-mentioned filling process, the air at the outer side of the second piston in each of the subpackage bottles is discharged via a hole in a rear cover, a filtration membrane and a hole in the gland while the pressure at the front end of the second piston is increased;

meanwhile, in the above-mentioned filling process, the air at the inner side of the second piston enters the subpackage bottle located at the tail end via the subpackage bottle located at the front end and the subpackage bottles located in the middle and is discharged via a first connection hose with a 0.2 µm-pore-size bacteriostatic filter while the pressure at the front end of the second piston is increased; in the process of discharging the air at the outer side and the inner side of the above-mentioned second piston, it can be ensured that the above-mentioned filling and air discharging are successfully performed at the same time; and after the above-mentioned filling is completed, the serum inside the subpackage bottles is finely adjusted under the action of the first spring so that the subpackage amounts of serum inside all the subpackage bottles are kept identical; and then, the first connection hose, a second connection hose and third connection hoses are subjected to heat sealing by a heat sealing machine to disassemble the subpackage bottles.

In the sterile preparation, subpackage and output system for serum and the method therefor according to the above-mentioned solutions, by disposing the blood collection and separation unit, the direct contact between the serum and the air can be reduced in the preparation and extraction processes, so that not only is the risk of contamination reduced, but also centrifugal separation may also be facilitated (a container body partially put in a centrifugal machine is over-sized or overhigh to affect the centrifugal separation effect); further, by cooperating the serum collection unit with the blood collection and separation unit, not only is the effect of reducing the direct contact between a sample and the air to reduce the risk of contamination achieved, but also the extraction process is more convenient and rapider, and misoperation is avoided; meanwhile, by disposing the liquid subpackage unit and cooperating the liquid subpackage unit with the serum collection unit, the precise quantitative distribution of the serum can be achieved, and when the serum needs to be put into cold storage or frozen, the structure of the liquid subpackage unit can be adjusted in real time, so that the phenomenon that a serum package is damaged is avoided, and the foundation is laid for the quantitative liquid output of the serum later; and by disposing the liquid boosting pen, the phenomenon that the serum is wasted can be effectively solved. The combination of the above-mentioned structures adopts sterile design, by which the investments of medical equipment can be effectively reduced, and the preparation cost and the use cost can be reduced; moreover, closed-loop sterile design is adopted in the overall preparation, extraction, subpackage, storage and use processes, so that the contact between the serum and the air can be effectively avoided to reduce the risk of contamination; the system and the method have the characteristics that the structure is simple, the overall process is simple and controllable, the safe and long-term storage of the serum is guaranteed, the waste of the serum and the blood drawing capacity are reduced, and the burden and negative emotion of a patient are relieved; and meanwhile, the device and the method provided by the present disclosure provide a standardized operation process, and therefore, not only is sterile operation achieved, but also the preparation time can be effectively shortened, and the foundation is laid for the industrialized and standardized preparation of the serum.

Figure 1:
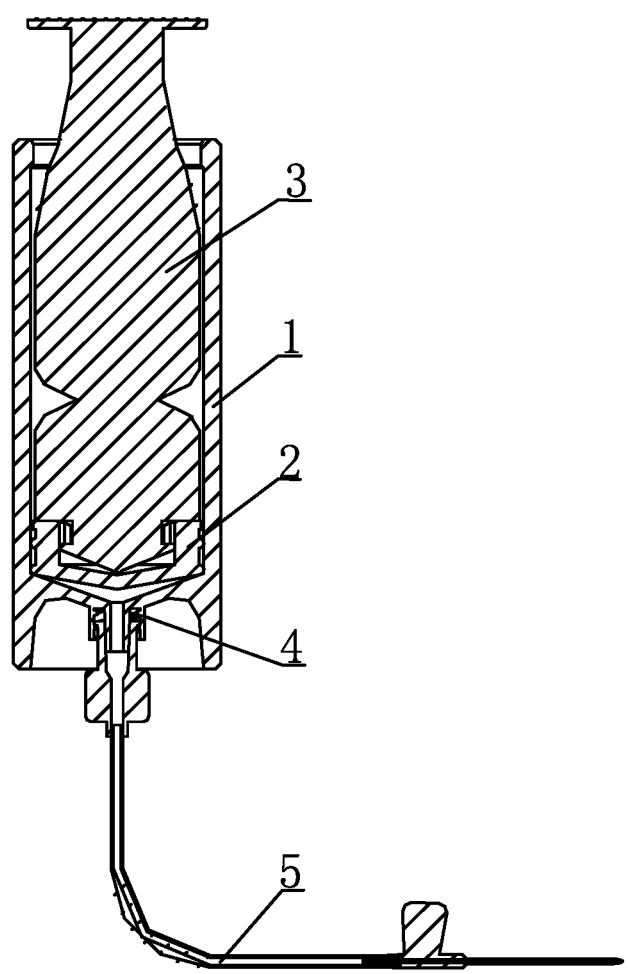
FIG. 1 is a structural schematic diagram of a blood collection and separation unit in the present disclosure.
Figure 2:
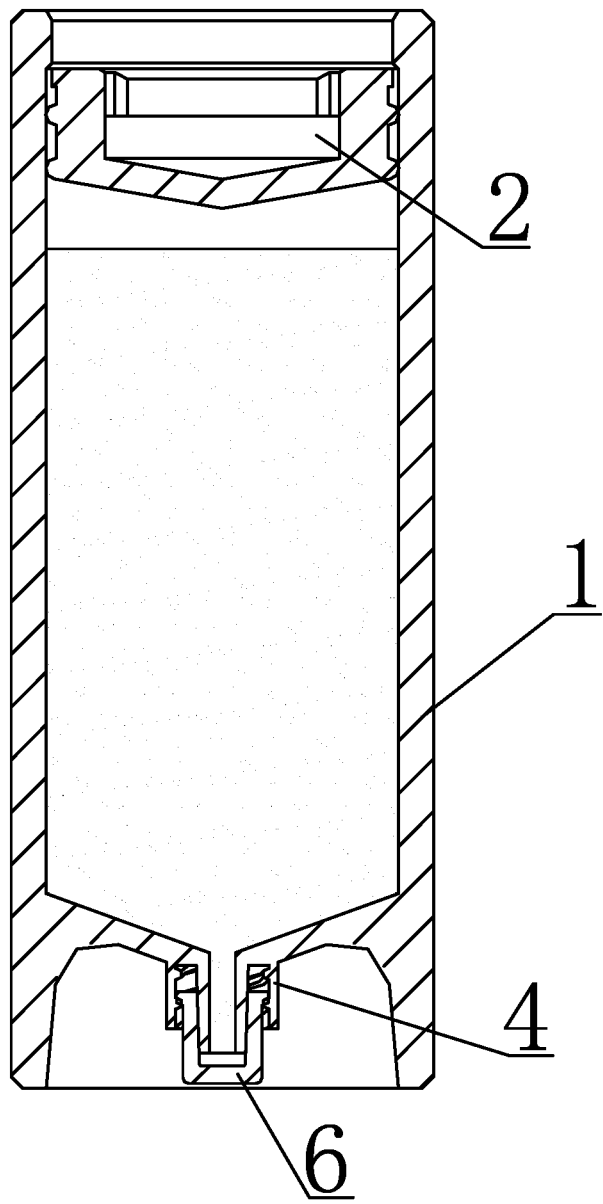
FIG. 2 is a structural schematic diagram of the blood collection and separation unit after whole blood is collected in the present disclosure.
Figure 3:
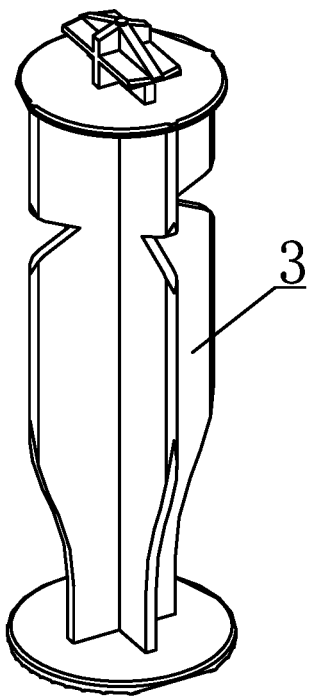
FIG. 3 is a structural schematic diagram of a push rod in the present disclosure.
Figure 4:
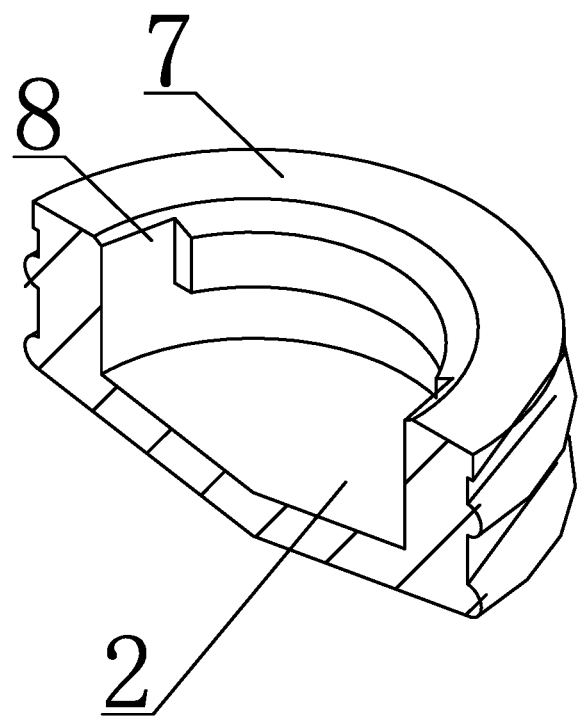
FIG. 4 is a structural schematic diagram of a first piston in the present disclosure.

In the drawings:
1. container main body; 2. first piston; 3. push rod; 4. first Luer taper; 5. blood collection needle; 6. end cap; 7. skirt part; 8. notch; 9. syringe; 10. injection needle; 11. needle seat; 12. medical tee; 13. subpackage bottle; 14. second Luer taper; 15. 0.2 µm-pore-size bacteriostatic filter; 16. first connection hose; 17. bottle body; 18. bottle cap; 19. rear cover; 20. second piston; 21; first spring; 22. gland; 23. hole; 24. filtration membrane; 25. graduation line; 26. connecting end; 27. second connection hose; 28. third connection hose; 29. pen cap; 30. pen body supporting tube; 31. adjustable rear cover; 32. ratchet tube; 33. push rod; 34. continuous ratchet teeth; 35. push rod positioning frame; 36. boosting frame; 37. button; 38. second spring; 39. first mounting rack; 40. positioning push rod; 41. boosting push rod; 42. second mounting rack; 43. groove; and 44. ratchet tube notch.

DETAILED DESCRIPTION OF THE EMBODIMENTS

In order to make the objectives, technical solutions and advantages of the embodiments of the present disclosure clearer, the technical solutions in the embodiments of the present disclosure will be clearly and completely described below with reference to the accompanying drawings in the embodiments of the present disclosure. Obviously, the described embodiments are merely part of embodiments of the present disclosure, rather than all of the embodiments. All other embodiments which are obtained by those of ordinary skill in the art based on the embodiments of the present disclosure without paying creative work fall within the protection scope of the present disclosure.

With reference to FIGS. 1 to 12, the present disclosure relates to a sterile preparation, subpackage and output system for serum and a method therefor. The system includes a blood collection and separation unit configured to collect venous blood and capable of achieving centrifugal separation of the blood; a serum collection unit cooperating with the blood collection and separation unit and configured to achieve sterile collection of serum; a liquid subpackage unit cooperating with the serum collection unit and configured to achieve precise sterile subpackage of the serum; and a liquid boosting pen configured to achieve precise and quantitative output of the serum. According to the present disclosure, by disposing the blood collection and separation unit, the collection of whole blood and the centrifugal separation of the whole blood can be achieved, and thus, the preparation of the serum is achieved; and in the preparation process, the collection and centrifugal separation of the whole blood are performed in the same container main body 1, by which not only is the operation facilitated and the contact between the whole blood and the air reduced, but also centrifugal separation can be directly performed on the whole blood (parts of existing container main bodies are larger in volume), so that the separation efficiency is effectively increased. Further, the blood collection and separation unit cooperates with the serum collection unit, by which the serum can be stably extracted, and the subpackage of the serum can be achieved, the above-mentioned extraction process is stable and reliable, and the closed-loop design for minimizing contact with superfluous medical equipment is adopted, so that the probability that the serum is contaminated is reduced. Furthermore, the serum collection unit cooperates with the liquid subpackage unit, by which the uniform subpackage for the serum can be achieved, which creates conditions for the later storage and use. By disposing the liquid subpackage unit, not only can the uniform subpackage of the serum be achieved, but also the volume inside the liquid subpackage unit can be autonomously adjusted according to the change of the volume of a liquid to avoid fracture caused by volume expansion, so that the purpose of long-term storage is achieved. By disposing the liquid boosting pen and combining the liquid boosting pen and subpackage bottles, not only can the use of the superfluous medical equipment be reduced, but also the quantitative delivery of the serum can be achieved, and therefore, the phenomenon that the serum is wasted in the use process is avoided.

With reference to FIGS. 1 to 4, the blood collection and separation unit includes a container main body 1, wherein an inner cavity of the container main body 1 is provided with a first piston 2 matched with the inner cavity, a detachable push rod 3 is disposed on the outer side of the first piston 2, a venous blood collection opening in the bottom of the container main body 1 is provided with a first Luer taper 4, and the first Luer taper 4 is provided with a blood collection needle 5 or an end cap 6 matched with the first Luer taper 4; and a skirt part 7 on the top end of the first piston 2 is provided with a notch 8, and the tail end of the push rod 3 is matched with the notch 8. By disposing the container main body 1, the collection of whole blood and the separation of serum from the whole blood can be achieved; when the blood collection needle 5 is used, the whole blood is collected; when the end cap 6 is used in the centrifugation process or serum collection process, leakage of the blood can be prevented; and further, by disposing the detachable push rod 3, the first piston 2 and the push rod 3 can be rapidly dismounted to achieve the purposes of collection and centrifugal separation of whole blood and serum collection in the container main body 1.

Figure 5:
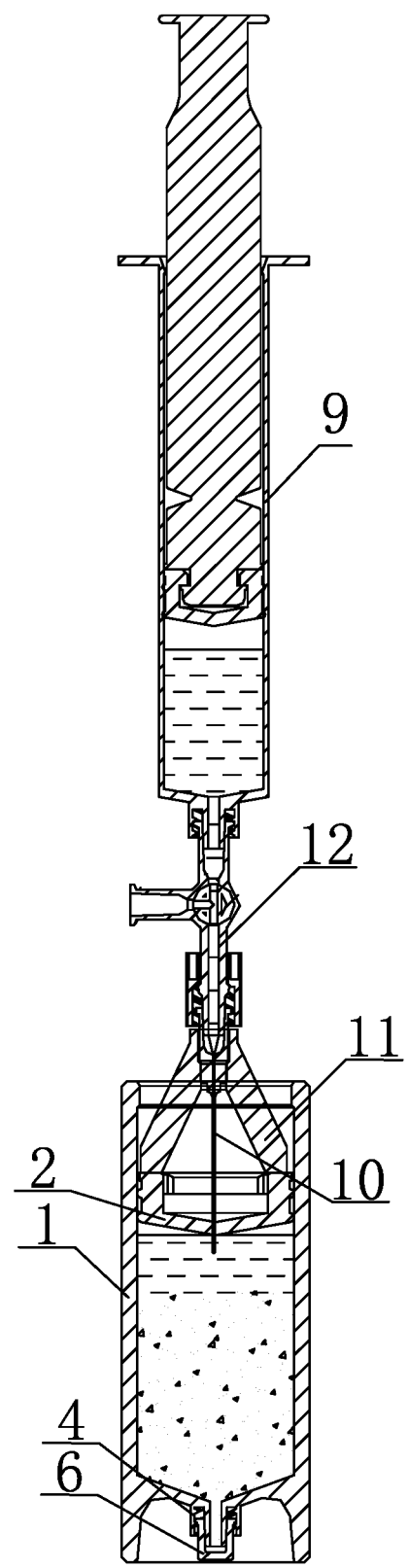
FIG. 5 is a structural schematic diagram of a serum collection unit extracting serum in the present disclosure.

With reference to FIG. 5, the serum collection unit includes a syringe 9 and a needle seat 11 used for supporting an injection needle 10, wherein the front end of the syringe 9 is connected to the injection needle 10 by a medical tee 12; the needle seat 11 is of an inverted funnel-shaped cavity structure of which the upper and lower bottom surfaces communicate; and a third end of the medical tee 12 is connected to the liquid subpackage unit. By disposing the medical tee 12, the purposes of serum collection and serum subpackage can be achieved; the medical tee 12 may be directly purchased on the market, so that the structure of the medical tee will not be repeated; the working process is that, when the medical tee 12 is used, it can be ensured that two ways are unclosed and the third way is closed, for example, in the process of collecting the serum, the syringe 9 communicates with the container main body 1, and the liquid subpackage unit does not communicate with the syringe 9 and the container main body 1; when the serum is subpackaged, the syringe 9 communicates with the liquid subpackage unit, and the container main body 1 does not communicate with the syringe 9 and the liquid subpackage unit; further, by disposing the needle seat 11, the process that the serum is extracted by using the injection needle 10 can be more convenient, rapier and stabler; and thus, the purpose of preventing impurities from entering the serum is achieved.

Figure 6:
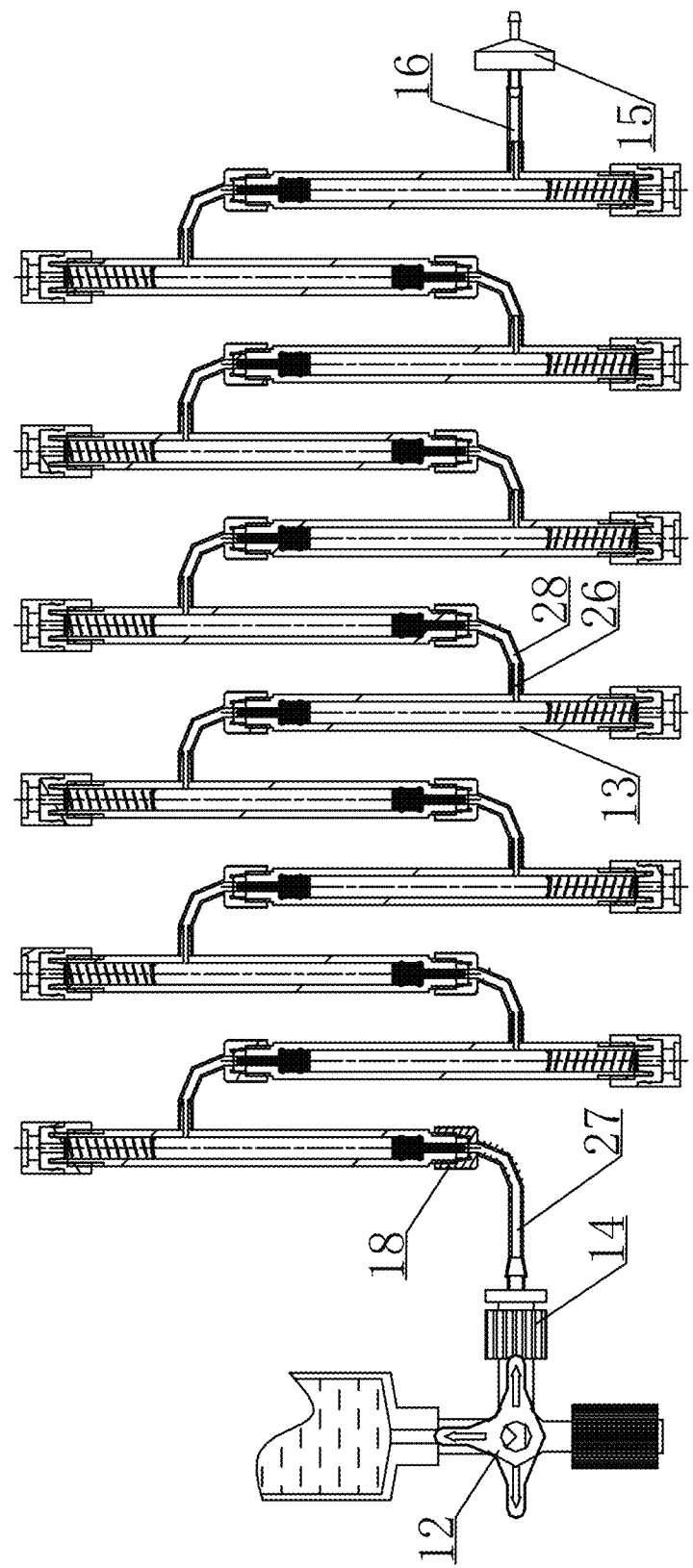
FIG. 6 is a structural schematic diagram of a liquid subpackage unit in the present disclosure.

With reference to FIG. 6, the liquid subpackage unit includes several subpackage bottles 13 that are connected in series; the subpackage bottle 13 located on the front end is connected to the third end of the medical tee 12 by a second Luer taper 14, and the subpackage bottle 13 located on the tail end is provided with a first connection hose 16 with a 0.2 μm-pore-size bacteriostatic filter 15. In the present disclosure, the liquid subpackage unit includes the several subpackage bottles 13 that are connected in series, and the first connection hose 16 with the 0.2 μm-pore-size bacteriostatic filter 15 on the subpackage bottle 13 located on the tail end is used for discharging air in the subpackage bottle 13 or the hose and stopping contaminants in the external air from entering the system.

Figure 7:
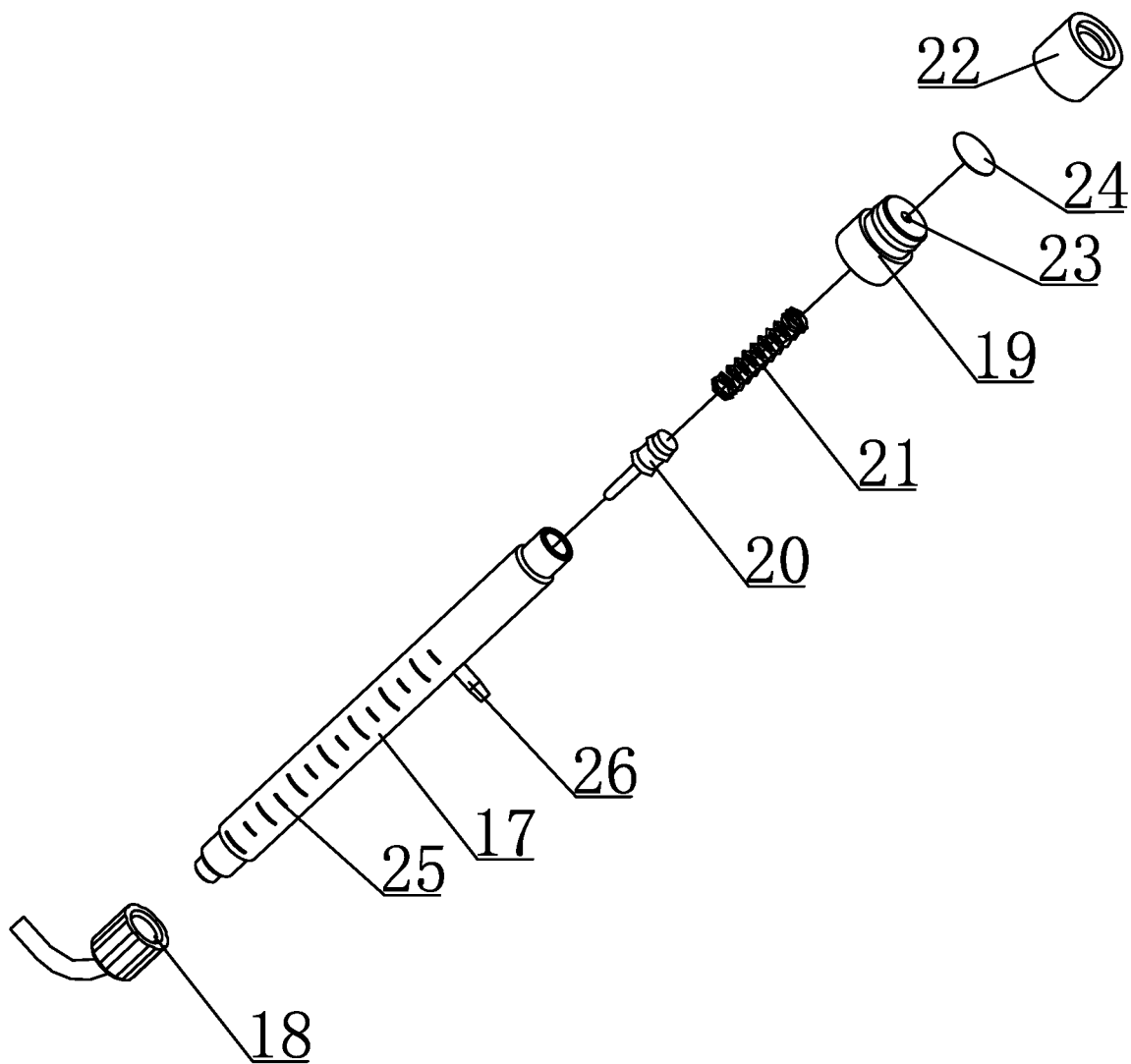
FIG. 7 is a structural schematic diagram of a subpackage bottle in the present disclosure.
Figure 8:
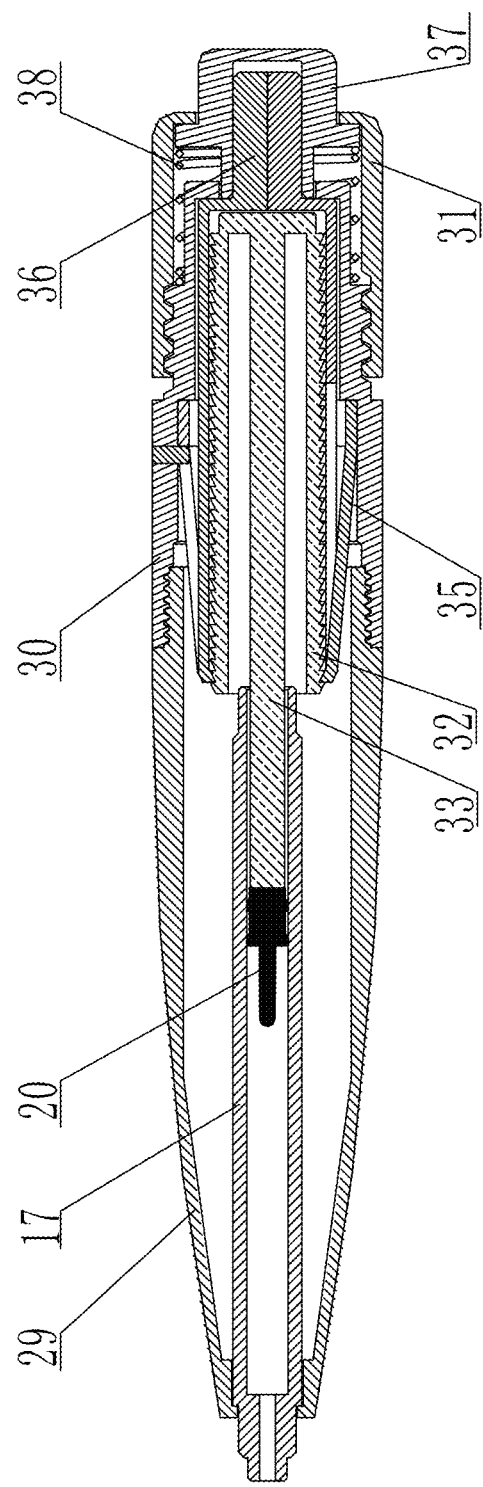
FIG. 8 is a structural schematic diagram of a liquid boosting pen in the present disclosure.
Figure 9:
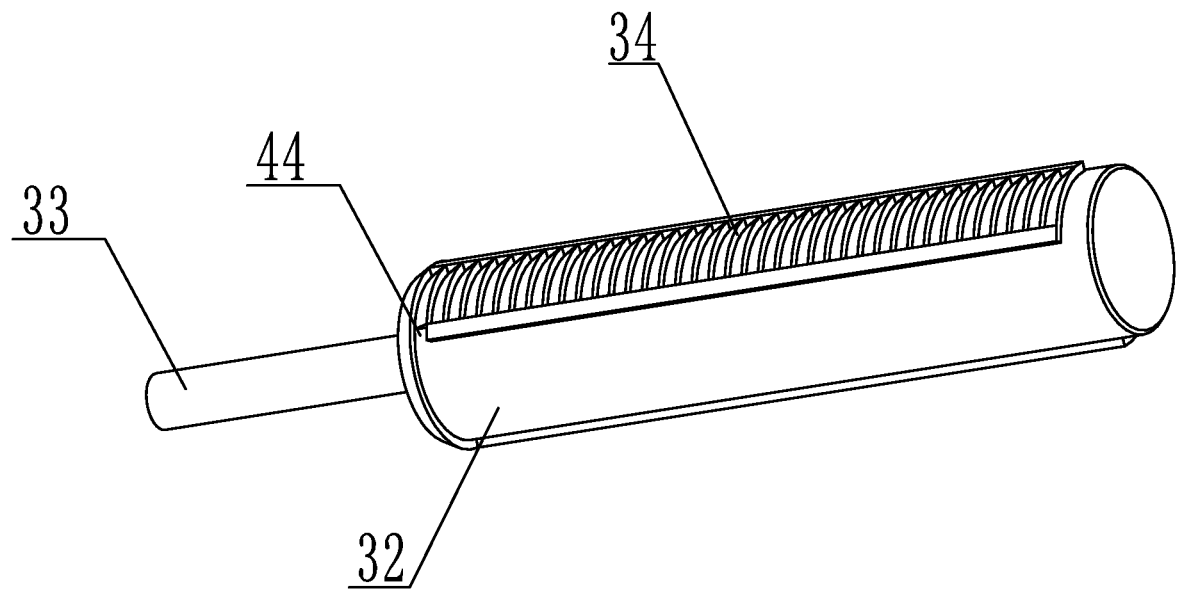
FIG. 9 is a structural schematic diagram of a ratchet tube in the present disclosure.
Figure 10:
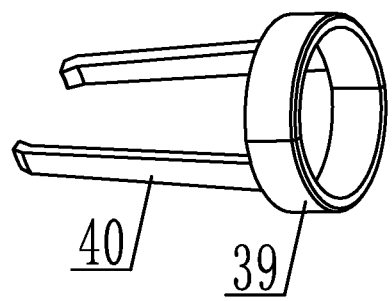
FIG. 10 is a structural schematic diagram of a push rod positioning frame in the present disclosure.
Figure 11:
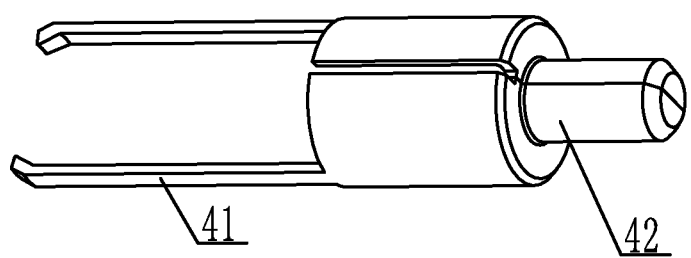
FIG. 11 is a structural schematic diagram of a boosting frame in the present disclosure.
Figure 12:
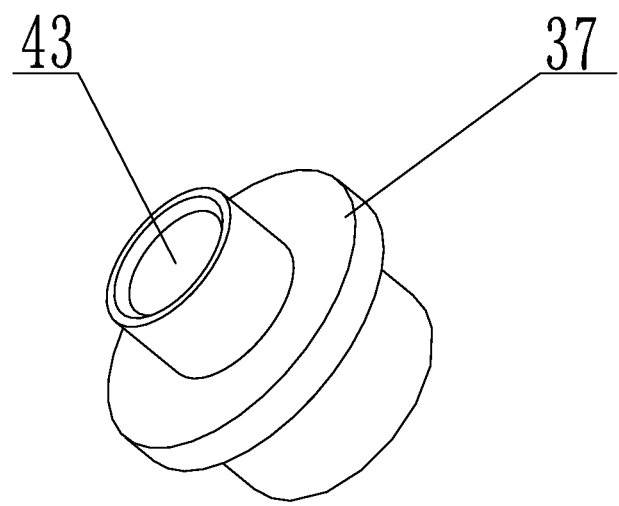
FIG. 12 is a structural schematic diagram of a button in the present disclosure.

With reference to FIGS. 6 to 7, the subpackage bottle 13 includes a bottle body 17, wherein the front end of the bottle body 17 is provided with a bottle cap 18, a rear cover 19 is screwed to the tail end of the bottle body 17, a second piston 20 is disposed inside the bottle body 17, and a first spring 21 is disposed between the second piston 20 and the rear cover 19; a gland 22 is screwed to the outer side of the rear cover 19, the rear cover 19 and the gland 22 are each provided with a hole 23, and a filtration membrane 24 is disposed between the rear cover 19 and the gland 22. In the present disclosure, the bottle cap 18 is used for liquid inlet, the volume inside the bottle body 17 can be adjusted through cooperation of the second piston 20 and the first spring 21, the adjustment for the volume not only can achieve the subpackage of the serum, but also can achieve adjustment for the internal volume during cold storage, thereby achieving the purpose of preventing the bottle body 17 from being fractured; and further, the holes 23 and the filtration membrane 24 disposed in the present disclosure can achieve the discharge of the air behind the second piston 20, so that the purpose of reducing the resistance to achieve the rapid subpackage of the serum is achieved.

With reference to FIGS. 6 to 7, graduation lines 25 are disposed between the front end and the tail end of the bottle body 17, and the part, corresponding to the tail ends of the graduation lines 25, of the bottle body 17 is provided with a connecting end 26; the bottle cap 18 of the subpackage bottle 13 located on the front end is connected to the second Luer taper 14 by a second connection hose 27; in two adjacent subpackage bottles 13, the connecting end 26 of the front subpackage bottle 13 is connected to the bottle cap 18 of the rear subpackage bottle 13 by a third connection hose 28; and the connecting end 26 of the subpackage bottle 13 located on the tail end is provided with the first connection hose 16 with the 0.2 µm-pore-size bacteriostatic filter 15. In the present disclosure, by using the graduation lines 25, the amount of the serum can be monitored, so that the amounts of the serum inside all the bottle bodies 17 are identical, and it is convenient to quantitatively use the serum when the serum is used later.

With reference to FIGS. 8 to 12, the liquid boosting pen includes a pen cap 29 and a pen body supporting tube 30 screwed to the tail end of the pen cap 29, and an adjustable rear cover 31 is screwed to the tail end of the pen body supporting tube 30; the bottle body 17 of the subpackage bottle 13 and the second piston 20 disposed inside the bottle body 17 are disposed inside the pen cap 29 and the pen body supporting tube 30, the second piston 20 is connected to a push rod 33 disposed inside a ratchet tube 32, continuous ratchet teeth 34 are disposed on the outer circumferential surface of the ratchet tube 32, a push rod positioning frame 35 and a boosting frame 36 are disposed inside the pen body supporting tube 30, the top of the boosting frame 36 is connected to a button 37, a second spring 38 is disposed between the button 37 and the pen body supporting tube 30, and the top end of the button 37 penetrates through the adjustable rear cover 31; the push rod positioning frame 35 includes a first mounting rack 39 that is snap-fitted in the pen body supporting tube 30, and positioning push rods 40 disposed on the bottom of the first mounting rack 39 and matched with the continuous ratchet teeth 34; the boosting frame 36 is disposed on the inner side of the push rod positioning frame 35 and includes boosting push rods 41 matched with the continuous ratchet teeth 34, and a second mounting rack 42 is disposed on the tops of the boosting push rods 41; and the front end of the bottle body 17 penetrates through the top of the pen cap 29. In the present disclosure, a refill between the pen cap 29 and the pen body supporting tube 30 adopts the subpackage bottle 13 in the serum subpackage process. The above-mentioned process not only can prevent the serum from being contaminated, but also can facilitate the operation. Meanwhile, in the present disclosure, the positioning push rods 40 and the boosting push rods 41 are disposed, the serum can quantitatively flow out of the bottle body 17 by means of the boosting push rods 41, and meanwhile, positioning is achieved by the positioning push rods 40, so that the purpose of restoring the boosting push rods 41 in time is achieved; and due to the cooperation between the above-mentioned positioning push rods 40 and boosting push rods 41, the serum can be quantitatively pushed out, and it can be ensured that the situation of waste is not easily caused in the process that the serum is used. In addition, in the present disclosure, the adjustable rear cover 31 is further disposed, and the distance between the adjustable rear cover 31 and the tail end of the pen body supporting tube 30 decides the delivery amount during quantitative output of the serum; and when the delivery amount needs to be adjusted, the adjustable rear cover 31 can be rotated to change the distance between the adjustable rear cover 31 and the tail end of the pen body supporting tube 30, preferably, the outer surfaces of the adjustable rear cover 31 and the pen body supporting tube 30 are provided with graduation or alignment lines, and when a liquid corresponds to the corresponding graduation or alignment lines, it is proven that the liquid output amounts are different, and thus, the purpose of facilitating adjustment of the liquid output amount is achieved.

With reference to FIGS. 8 to 12, the continuous ratchet teeth 34 are disposed on the two corresponding sides of the outer circumferential surface of the ratchet tube 32, the push rod positioning frame 35 includes the two positioning push rods 40 respectively matched with the continuous ratchet teeth 34 located on the two sides, and the boosting frame 36 includes the two boosting push rods 41 respectively matched with the continuous ratchet teeth 34 located on the two sides; a groove 43 is disposed at the bottom end of the button 37, and the second mounting rack 42 is snap-fitted in the groove; and a ratchet tube notch 44 is disposed on one side of the lower parts of the continuous ratchet teeth 34. The ratchet tube notch 44 in the present disclosure can facilitate the entrance or exit of the positioning push rods 40 and the boosting push rods 41, so that the purpose of rapidly assembling the positioning push rods 40 and the boosting push rods 41 after the bottle body 17 is replaced is achieved.

The present disclosure further provides a method for a sterile preparation, subpackage and output system for serum, and the method includes the following steps:

step 1: connecting a push rod 3 to a first piston 2, enabling a blood collection needle 5 to be fixedly connected to a first Luer taper 4, and after the connection is completed, collecting venous blood;

step 2: after the collection of the venous blood is completed, dismounting the blood collection needle 5 from the first Luer taper 4, and mounting an end cap 6; and dismounting the push rod 3 from the first piston 2;

step 3: after the push rod 3 and the blood collection needle 5 are dismounted and the end cap 6 is mounted, incubating and centrifuging whole blood in a container main body 1, and layering centrifuged erythrocytes and serum, wherein the serum is a supernate;

step 4: placing a needle seat 11 which is of an inverted funnel-shaped cavity structure at the outer side of the first piston 2, and enabling an injection needle 10 to penetrate through the upper bottom surface of the needle seat 11, the lower bottom surface of the needle seat 11 and the first piston 2 to enter the serum serving as the supernate;

step 5: adjusting a medical tee 12 to enable a cavity of a syringe 9 to communicate with the container main body 1, and pressing a barrel of the syringe 9 to enable the serum serving as the supernate to enter the cavity of the syringe 9 via the container main body 1, the injection needle 10 and the medical tee 12;

step 6: adjusting the medical tee 12 to enable the cavity of the syringe 9 to communicate with a liquid subpackage unit, and boosting a pull rod of the syringe 9 to enable the serum inside the cavity of the syringe 9 to enter the liquid subpackage unit via the medical tee 12;

step 7: after enabling the serum inside the cavity of the syringe 9 to enter the liquid subpackage unit in step 6 is completed, completing subpackage; and after the subpackage is completed, disassembling the liquid subpackage unit into several subpackage bottles 13, and performing storage in a low-temperature or freezing manner;

step 8: when the serum needs to be used, enabling positioning push rods 40 and boosting push rods 41 to be matched with ratchet teeth located on the same position on a ratchet tube 32; putting a bottle body 17 into a pen cap 29, and connecting a push rod 33 inside the ratchet tube 32 to a second piston 20 in the bottle body 17; and meanwhile, screwing the pen cap 29 to a pen body supporting tube 30, mounting a second spring 38 and a button 37, and finally, screwing an adjustable rear cover 31 to the pen body supporting tube 30;

step 9: placing the bottle body 17 on the top of the pen cap 29 above a position where the serum needs to be dripped, manually pressing the button 37, driving, by the button 37, a boosting frame 36 to move towards the pen cap 29 end, pushing, by the top ends of the boosting push rods 41, the ratchet tube 32 to advance via the ratchet teeth, and pushing, by the push rod 33 in the ratchet tube 32, the second piston 20 to move towards the front end of the bottle body 17 to quantitatively output the serum;

step 10: when the above-mentioned boosting push rods 41 push the ratchet tube 32 to advance, keeping the positions of the positioning push rods 40 unchanged, and enabling the top ends of the positioning push rods 40 to enter the next ratchet teeth of continuous ratchet teeth 34; after the quantitative output of the serum is completed, releasing the button 37 to enable the button 37 to be restored under the action of the second spring 38, keeping the positions of the positioning push rods 40 for fixing the ratchet tube 32 unchanged in a restoring process, and enabling the boosting push rods 41 to be restored under the driving of the button 37 and enter the same ratchet teeth which the top ends of the positioning push rods 40 enter, thus completing the overall process of quantitative output of the serum;

step 11: after the serum in one subpackage bottle 13 is used up, replacing the subpackage bottle 13 with a new subpackage bottle 13, wherein top ends of the positioning push rods 40 and the boosting push rods 41 may enter the continuous ratchet teeth 34 via ratchet tube notches 44 during replacement; and step 12: disposing an external thread on the outer circumferential surface of the tail end of the pen body supporting tube 30, connecting the external thread on the tail end of the pen body supporting tube 30 to an internal thread of the adjustable rear cover 31, and adjusting the stroke of the second spring 38 by adjusting the distance between the pen body supporting tube 30 and the adjustable rear cover 31; wherein the shorter the stroke of the second spring 38, the smaller the amount of the serum output every time, and the longer the stroke of the second spring 38, the greater the amount of the serum output every time. It needs to be noted that the stroke of the second spring 38 in the step is preferably adjusted to be an integral multiple of the distance between the adjacent ratchet teeth, that is, the stroke of the second spring 38 is: n+a, n+2a, n+3a, etc., and the above-mentioned n is the shortest stroke of the second spring 38, and a is the distance between the adjacent ratchet teeth.

Preferably, the specific process of enabling the serum inside the cavity of the syringe 9 to enter the liquid subpackage unit via the medical tee 12 in the step 6 is that: the pull rod of the syringe 9 is boosted to enable the serum inside the syringe 9 to enter the subpackage bottle 13 located on the front end, the pressure inside the subpackage bottle 13 is increased, the second piston 20 is pushed to move towards a gland 22 side while the pressure is increased, and when the second piston 20 moves to a first spring 21, a connecting end 26 is opened; after the connecting end 26 is opened, the serum inside the syringe 9 continuously enters the subpackage bottle 13 located on the front end, and the second piston 20 causes the connecting end 26 to be completely opened under the pressure of the serum and the serum enters the next subpackage bottle 13; and after filling of all the serum inside the syringe 9 is completed, the subpackage process is ended;

in the above-mentioned filling process, the air at the outer side of the second piston 20 in each of the subpackage bottles 13 is discharged via a hole 23 in a rear cover 19, a filtration membrane 24 and a hole 23 in the gland 22 while the pressure at the front end of the second piston 20 is increased; meanwhile, in the above-mentioned filling process, the air at the inner side of the second piston 20 enters the subpackage bottle 13 located at the tail end via the subpackage bottle 13 located at the front end and the subpackage bottles 13 located in the middle and is discharged via a first connection hose 16 with a 0.2 μm-pore-size bacteriostatic filter 15 while the pressure at the front end of the second piston 20 is increased; in the process of discharging the air at the outer side and the inner side of the above-mentioned second piston 20, it can be ensured that the above-mentioned filling and air discharging are successfully performed at the same time; and after the above-mentioned filling is completed, the serum inside the subpackage bottles 13 is finely adjusted under the action of the first spring 21 so that the subpackage amounts of serum inside all the subpackage bottles 13 are kept identical; and then, the first connection hose 16, a second connection hose 27 and third connection hoses 28 are subjected to heat sealing by a heat sealing machine to disassemble the subpackage bottles 13.

The blood collection and separation unit, the serum collection unit, the liquid subpackage unit and the liquid boosting pen provided in the present disclosure jointly constitute an integral technical solution by which whole blood collection, centrifugal preparation, serum extraction, serum subpackage and storage as well as quantitative use of the serum can be achieved as a whole. Closed-loop sterile design is adopted in the above-mentioned process, so that the contact between the serum (or whole blood) and the air can be effectively avoided to reduce the risk of contamination; and a standardized operation process is provided, and therefore, not only is sterile operation achieved, but also the preparation time can be effectively shortened, and the foundation is laid for the industrialized and standardized preparation of the serum. Meanwhile, for each of the above-mentioned units, the blood collection and separation unit can achieve whole blood collection and the centrifugal preparation of the serum, the serum collection unit can achieve the serum collection and cooperate for serum subpackage, the liquid subpackage unit not only can achieve the uniform subpackage of the serum and long-term storage under the condition that the volume of the serum is changed, but also can be used as a refill of the liquid boosting pen; and further, the liquid boosting pen has the characteristics that the quantitative output of the serum can be achieved, not only is the usage amount of the serum reduced, but also the frequency of drawing blood and performing centrifugal separation by using the blood collection and separation unit can be reduced, meanwhile, the blood volume can be effectively reduced, and the burden and negative emotion of a patient are relieved. By using the above-mentioned equipment, the preparation and extraction, the subpackage and cold storage as well as the use of the serum form a whole, the structure is simple, the overall process is simple and controllable, the sterile operation for the serum is achieved, the safe and long-term storage of the serum is guaranteed, the waste of the serum is reduced, and the foundation is laid for the industrialized and standardized preparation of the serum.

In order to explain the present disclosure in more detail, the present disclosure will now be further described in combination with embodiments. Specific embodiments are shown as follows.

Embodiment 1

Provided is a sterile preparation, subpackage and output system for serum, wherein the system includes: a blood collection and separation unit configured to collect venous blood and capable of achieving centrifugal separation of the blood; a serum collection unit cooperating with the blood collection and separation unit and configured to achieve sterile collection of serum; a liquid subpackage unit cooperating with the serum collection unit and configured to achieve precise sterile subpackage of the serum; and a liquid boosting pen configured to achieve precise quantitative output of the serum.

Further, the blood collection and separation unit includes a container main body 1, wherein an inner cavity of the container main body 1 is provided with a first piston 2 matched with the inner cavity, a detachable push rod 3 is disposed on the outer side of the first piston 2, a venous blood collection opening in the bottom of the container main body 1 is provided with a first Luer taper 4, and the first Luer taper 4 is provided with a blood collection needle 5 or an end cap 6 matched with the first Luer taper 4; and a skirt part 7 on the top end of the first piston 2 is provided with a notch 8, and the tail end of the push rod 3 is matched with the notch 8.

Further, the serum collection unit includes a syringe 9 and a needle seat 11 used for supporting an injection needle 10, wherein the front end of the syringe 9 is connected to the injection needle 10 by a medical tee 12; the needle seat 11 is of an inverted funnel-shaped cavity structure of which the upper and lower bottom surfaces communicate; and a third end of the medical tee 12 is connected to the liquid subpackage unit.

Further, the liquid subpackage unit includes several subpackage bottles 13 that are connected in series; the subpackage bottle 13 located on the front end is connected to the third end of the medical tee 12 by a second Luer taper 14, and the subpackage bottle 13 located on the tail end is provided with a first connection hose 16 with a 0.2 µm-pore-size bacteriostatic filter 15.

Further, each of the subpackage bottles 13 includes a bottle body 17, wherein the front end of the bottle body 17 is provided with a bottle cap 18, a rear cover 19 is screwed to the tail end of the bottle body 17, a second piston 20 is disposed inside the bottle body 17, and a first spring 21 is disposed between the second piston 20 and the rear cover 19; a gland 22 is screwed to the outer side of the rear cover 19, the rear cover 19 and the gland 22 are each provided with a hole 23, and a filtration membrane 24 is disposed between the rear cover 19 and the gland 22.

Further, graduation lines 25 are disposed between the front end and the tail end of the bottle body 17, and the part, corresponding to the tail ends of the graduation lines 25, of the bottle body 17 is provided with a connecting end 26; the bottle cap 18 of the subpackage bottle 13 located on the front end is connected to the second Luer taper 14 by a second connection hose 27; in two adjacent subpackage bottles 13, the connecting end 26 of the front subpackage bottle 13 is connected to the bottle cap 18 of the rear subpackage bottle 13 by a third connection hose 28; and the connecting end 26 of the subpackage bottle 13 located on the tail end is provided with the first connection hose 16 with the 0.2 µm-pore-size bacteriostatic filter 15.

Further, the liquid boosting pen includes a pen cap 29 and a pen body supporting tube 30 screwed to the tail end of the pen cap 29, and an adjustable rear cover 31 is screwed to the tail end of the pen body supporting tube 30; the bottle body 17 of the subpackage bottle 13 and the second piston 20 disposed inside the bottle body 17 are disposed inside the pen cap 29 and the pen body supporting tube 30, the second piston 20 is connected to a push rod 33 disposed inside a ratchet tube 32, continuous ratchet teeth 34 are disposed on the outer circumferential surface of the ratchet tube 32, a push rod positioning frame 35 and a boosting frame 36 are disposed inside the pen body supporting tube 30, the top of the boosting frame 36 is connected to a button 37, a second spring 38 is disposed between the button 37 and the pen body supporting tube 30, and the top end of the button 37 penetrates through the adjustable rear cover 31; the push rod positioning frame 35 includes a first mounting rack 39 that is snap-fitted in the pen body supporting tube 30, and positioning push rods 40 disposed on the bottom of the first mounting rack 39 and matched with the continuous ratchet teeth 34; the boosting frame 36 is disposed on the inner side of the push rod positioning frame 35 and includes boosting push rods 41 matched with the continuous ratchet teeth 34, and a second mounting rack 42 is disposed on the tops of the boosting push rods 41; and the front end of the bottle body 17 penetrates through the top of the pen cap 29.

Further, the continuous ratchet teeth 34 are disposed on the two corresponding sides of the outer circumferential surface of the ratchet tube 32, the push rod positioning frame 35 includes the two positioning push rods 40 respectively matched with the continuous ratchet teeth 34 located on the two sides, and the boosting frame 36 includes the two boosting push rods 41 respectively matched with the continuous ratchet teeth 34 located on the two sides; a groove 43 is disposed at the bottom end of the button 37, and the second mounting rack 42 is snap-fitted in the groove; and a ratchet tube notch 44 is disposed on one side of the lower parts of the continuous ratchet teeth 34.

The present disclosure further provides a method for a sterile preparation, subpackage and output system for serum, and the method includes the following steps:
  step 1: connecting a push rod 3 to a first piston 2, enabling a blood collection needle 5 to be fixedly connected to a first Luer taper 4, and after the connection is completed, collecting venous blood;
  step 2: after the collection of the venous blood is completed, dismounting the blood collection needle 5 from the first Luer taper 4, and mounting an end cap 6; and dismounting the push rod 3 from the first piston 2;

step 3: after the push rod 3 and the blood collection needle 5 are dismounted and the end cap 6 is mounted, incubating and centrifuging whole blood in a container main body 1, and layering centrifuged erythrocytes and serum, wherein the serum is a supernate;

step 4: placing a needle seat 11 which is of an inverted funnel-shaped cavity structure at the outer side of the first piston 2, and enabling an injection needle 10 to penetrate through the upper bottom surface of the needle seat 11, the lower bottom surface of the needle seat 11 and the first piston 2 to enter the serum serving as the supernate;

step 5: adjusting a medical tee 12 to enable a cavity of a syringe 9 to communicate with the container main body 1, and a barrel of the syringe 9 is pressed to enable the serum serving as the supernate to enter the cavity of the syringe 9 via the container main body 1, the injection needle 10 and the medical tee 12;

step 6: adjusting the medical tee 12 to enable the cavity of the syringe 9 to communicate with a liquid subpackage unit, and boosting a pull rod of the syringe 9 to enable the serum inside the cavity of the syringe 9 to enter the liquid subpackage unit via the medical tee 12;

step 7: after enabling the serum inside the cavity of the syringe 9 to enter the liquid subpackage unit in step 6 is completed, completing subpackage; and after the subpackage is completed, disassembling the liquid subpackage unit into several subpackage bottles 13, and performing storage in a low-temperature or freezing manner;

step 8: when the serum needs to be used, enabling positioning push rods 40 and boosting push rods 41 to be matched with ratchet teeth located on the same position on a ratchet tube 32; putting a bottle body 17 into a pen cap 29, and connecting a push rod 33 inside the ratchet tube 32 to a second piston 20 in the bottle body 17; and meanwhile, screwing the pen cap 29 to a pen body supporting tube 30, mounting a second spring 38 and a button 37, and finally, screwing an adjustable rear cover 31 to the pen body supporting tube 30;

step 9: placing the bottle body 17 on the top of the pen cap 29 above a position where the serum needs to be dripped, manually pressing the button 37, driving, by the button 37, a boosting frame 36 to move towards the pen cap 29 end, pushing, by the top ends of the boosting push rods 41, the ratchet tube 32 to advance via the ratchet teeth, and pushing, by the push rod 33 in the ratchet tube 32, the second piston 20 to move towards the front end of the bottle body 17 to quantitatively output the serum;

step 10: when the above-mentioned boosting push rods 41 push the ratchet tube 32 to advance, keeping the positions of the positioning push rods 40 unchanged, and enabling the top ends of the positioning push rods 40 to enter the next ratchet teeth of continuous ratchet teeth 34; after the quantitative output of the serum is completed, releasing the button 37 to enable the button 37 to be restored under the action of the second spring 38, keeping the positions of the positioning push rods 40 for fixing the ratchet tube 32 unchanged in a restoring process, and enabling the boosting push rods 41 to be restored under the driving of the button 37 and enter the same ratchet teeth which the top ends of the positioning push rods 40 enter, thus completing the overall process of quantitative output of the serum;

step 11: after the serum in one subpackage bottle 13 is used up, replacing the subpackage bottle 13 with a new subpackage bottle 13, wherein top ends of the positioning push rods 40 and the boosting push rods 41 may enter the continuous ratchet teeth 34 via ratchet tube notches 44 during replacement; and step 12: disposing an external thread on the outer circumferential surface of the tail end of the pen body supporting tube 30, connecting the external thread on the tail end of the pen body supporting tube 30 to an internal thread of the adjustable rear cover 31, and adjusting the stroke of the second spring 38 by adjusting the distance between the pen body supporting tube 30 and the adjustable rear cover 31; wherein the shorter the stroke of the second spring 38, the smaller the amount of the serum output every time, and the longer the stroke of the second spring 38, the greater the amount of the serum output every time.

Embodiment 2

Provided is a sterile preparation, subpackage and output system for serum, wherein the system includes: a blood collection and separation unit configured to collect venous blood and capable of achieving centrifugal separation of blood; a serum collection unit cooperating with the blood collection and separation unit and configured to achieve sterile collection of serum; a liquid subpackage unit cooperating with the serum collection unit and configured to achieve precise sterile subpackage of the serum; and a liquid boosting pen configured to achieve precise quantitative output of the serum.

Further, the blood collection and separation unit includes a container main body 1, wherein an inner cavity of the container main body 1 is provided with a first piston 2 matched with the inner cavity, a detachable push rod 3 is disposed on the outer side of the first piston 2, a venous blood collection opening in the bottom of the container main body 1 is provided with a first Luer taper 4, and the first Luer taper 4 is provided with a blood collection needle 5 or an end cap 6 matched with the first Luer taper 4; and a skirt part 7 on the top end of the first piston 2 is provided with a notch 8, and the tail end of the push rod 3 is matched with the notch 8.

Further, the serum collection unit includes a syringe 9 and a needle seat 11 used for supporting an injection needle 10, wherein the front end of the syringe 9 is connected to the injection needle 10 by a medical tee 12; the needle seat 11 is of an inverted funnel-shaped cavity structure of which the upper and lower bottom surfaces communicate; and a third end of the medical tee 12 is connected to the liquid subpackage unit.

Further, the liquid subpackage unit includes several subpackage bottles 13 that are connected in series; the subpackage bottle 13 located on the front end is connected to the third end of the medical tee 12 by a second Luer taper 14, and the subpackage bottle 13 located on the tail end is provided with a first connection hose 16 with a 0.2 μm-pore-size bacteriostatic filter 15.

Further, each of the subpackage bottles 13 includes a bottle body 17, wherein the front end of the bottle body 17 is provided with a bottle cap 18, a rear cover 19 is screwed to the tail end of the bottle body 17, a second piston 20 is disposed inside the bottle body 17, and a first spring 21 is disposed between the second piston 20 and the rear cover 19; a gland 22 is screwed to the outer side of the rear cover 19, the rear cover 19 and the gland 22 are each provided with a hole 23, and a filtration membrane 24 is disposed between the rear cover 19 and the gland 22.

Further, graduation lines 25 are disposed between the front end and the tail end of the bottle body 17, and the part, corresponding to the tail ends of the graduation lines 25, of the bottle body 17 is provided with a connecting end 26; the bottle cap 18 of the subpackage bottle 13 located on the front end is connected to the second Luer taper 14 by a second connection hose 27; in two adjacent subpackage bottles 13, the connecting end 26 of the front subpackage bottle 13 is connected to the bottle cap 18 of the rear subpackage bottle 13 by a third connection hose 28; and the connecting end 26 of the subpackage bottle 13 located on the tail end is provided with the first connection hose 16 with the 0.2 μm-pore-size bacteriostatic filter 15.

Further, the liquid boosting pen includes a pen cap 29 and a pen body supporting tube 30 screwed to the tail end of the pen cap 29, and an adjustable rear cover 31 is screwed to the tail end of the pen body supporting tube 30; the bottle body 17 of the subpackage bottle 13 and the second piston 20 disposed inside the bottle body 17 are disposed inside the pen cap 29 and the pen body supporting tube 30, the second piston 20 is connected to a push rod 33 disposed inside a ratchet tube 32, continuous ratchet teeth 34 are disposed on the outer circumferential surface of the ratchet tube 32, a push rod positioning frame 35 and a boosting frame 36 are disposed inside the pen body supporting tube 30, the top of the boosting frame 36 is connected to a button 37, a second spring 38 is disposed between the button 37 and the pen body supporting tube 30, and the top end of the button 37 penetrates through the adjustable rear cover 31; the push rod positioning frame 35 includes a first mounting rack 39 that is snap-fitted in the pen body supporting tube 30, and positioning push rods 40 disposed on the bottom of the first mounting rack 39 and matched with the continuous ratchet teeth 34; the boosting frame 36 is disposed on the inner side of the push rod positioning frame 35 and includes boosting push rods 41 matched with the continuous ratchet teeth 34, and a second mounting rack 42 is disposed on the tops of the boosting push rods 41; and the front end of the bottle body 17 penetrates through the top of the pen cap 29.

Further, the continuous ratchet teeth 34 are disposed on the two corresponding sides of the outer circumferential surface of the ratchet tube 32, the push rod positioning frame 35 includes the two positioning push rods 40 respectively matched with the continuous ratchet teeth 34 located on the two sides, and the boosting frame 36 includes the two boosting push rods 41 respectively matched with the continuous ratchet teeth 34 located on the two sides; a groove 43 is disposed at the bottom end of the button 37, and the second mounting rack 42 is snap-fitted in the groove; and a ratchet tube notch 44 is disposed on one side of the lower parts of the continuous ratchet teeth 34.

The present disclosure further provides a method for a sterile preparation, subpackage and output system for serum, and the method includes the following steps:

step 1: connecting a push rod 3 to a first piston 2, enabling a blood collection needle 5 to be fixedly connected to a first Luer taper 4, and after the connection is completed, collecting venous blood;

step 2: after the collection of the venous blood is completed, dismounting the blood collection needle 5 from the first Luer taper 4, and mounting an end cap 6; and dismounting the push rod 3 from the first piston 2;

step 3: the push rod 3 and the blood collection needle 5 are dismounted and the end cap 6 is mounted, incubating and centrifuging whole blood in a container main body 1, and layering centrifuged erythrocytes and serum, wherein the serum is a supernate;

step 4: placing a needle seat 11 which is of an inverted funnel-shaped cavity structure at the outer side of the first piston 2, and enabling an injection needle 10 to penetrate through the upper bottom surface of the needle seat 11, the lower bottom surface of the needle seat 11 and the first piston 2 to enter the serum serving as the supernate;

step 5: adjusting a medical tee 12 to enable a cavity of a syringe 9 to communicate with the container main body 1, and pressing a barrel of the syringe 9 to enable the serum serving as the supernate to enter the cavity of the syringe 9 via the container main body 1, the injection needle 10 and the medical tee 12;

step 6: adjusting the medical tee 12 to enable the cavity of the syringe 9 to communicate with a liquid subpackage unit, and boosting a pull rod of the syringe 9 to enable the serum inside the cavity of the syringe 9 to enter the liquid subpackage unit via the medical tee 12;

step 7: after enabling the serum inside the cavity of the syringe 9 to enter the liquid subpackage unit in step 6 is completed, completing subpackage; and after the subpackage is completed, disassembling the liquid subpackage unit into several subpackage bottles 13, and performing storage in a low-temperature or freezing manner;

step 8: when the serum needs to be used, enabling positioning push rods 40 and boosting push rods 41 to be matched with ratchet teeth located on the same position on a ratchet tube 32; putting a bottle body 17 into a pen cap 29, and connecting a push rod 33 inside the ratchet tube 32 to a second piston 20 in the bottle body 17; and meanwhile, screwing the pen cap 29 to a pen body supporting tube 30, mounting a second spring 38 and a button 37, and finally, screwing an adjustable rear cover 31 to the pen body supporting tube 30;

step 9: placing the bottle body 17 on the top of the pen cap 29 above a position where the serum needs to be dripped, manually pressing the button 37, driving, by the button 37, a boosting frame 36 to move towards the pen cap 29 end, pushing, by the top ends of the boosting push rods 41, the ratchet tube 32 to advance via the ratchet teeth, and pushing, by the push rod 33 in the ratchet tube 32, the second piston 20 to move towards the front end of the bottle body 17 to quantitatively output the serum;

step 10: when the above-mentioned boosting push rods 41 push the ratchet tube 32 to advance, keeping the positions of the positioning push rods 40 unchanged, and enabling the top ends of the positioning push rods 40 to enter the next ratchet teeth of continuous ratchet teeth 34; after the quantitative output of the serum is completed, releasing the button 37 to enable the button 37 to be restored under the action of the second spring 38, keeping the positions of the positioning push rods 40 for fixing the ratchet tube 32 unchanged in a restoring process, and enabling the boosting push rods 41 to be restored under the driving of the button 37 and enter the same ratchet teeth which the top ends of the positioning push rods 40 enter, thus, completing the overall process of quantitative output of the serum;

step 11: after the serum in one subpackage bottle 13 is used up, replacing the subpackage bottle 13 with a new subpackage bottle 13, wherein top ends of the positioning push rods 40 and the boosting push rods 41 may enter the continuous ratchet teeth 34 via ratchet tube notches 44 during replacement; and step 12: disposing an external thread on the outer circumferential surface of the tail end of the pen body supporting tube 30, connecting the external thread on the tail end of the pen body supporting tube 30 to an internal thread of the adjustable rear cover 31, and adjusting the stroke of the second spring 38 by adjusting the distance between the pen body supporting tube 30 and the adjustable rear cover 31; wherein the shorter the stroke of the second spring 38, the smaller the amount of the serum output every time, and the longer the stroke of the second spring 38, the greater the amount of the serum output every time.

Further, the specific process of enabling the serum inside the cavity of the syringe 9 to enter the liquid subpackage unit via the medical tee 12 in the step 6 is that: the pull rod of the syringe 9 is boosted to enable the serum inside the syringe 9 to enter the subpackage bottle 13 located on the front end, the pressure inside the subpackage bottle 13 is increased, the second piston 20 is pushed to move towards a gland 22 side while the pressure is increased, and when the second piston 20 moves to a first spring 21, a connecting end 26 is opened; after the connecting end 26 is opened, the serum inside the syringe 9 continuously enters the subpackage bottle 13 located on the front end, and the second piston 20 causes the connecting end 26 to be completely opened under the pressure of the serum and the serum enters the next subpackage bottle 13; and after filling of all the serum inside the syringe 9 is completed, the subpackage process is ended;

in the above-mentioned filling process, the air at the outer side of the second piston 20 in each of the subpackage bottles 13 is discharged via a hole 23 in a rear cover 19, a filtration membrane 24 and a hole 23 in the gland 22 while the pressure at the front end of the second piston 20 is increased; meanwhile, in the above-mentioned filling process, the air at the inner side of the second piston 20 enters the subpackage bottle 13 located at the tail end via the subpackage bottle 13 located at the front end and the subpackage bottles 13 located in the middle and is discharged by a first connection hose 16 with a 0.2 μm-pore-size bacteriostatic filter 15 while the pressure at the front end of the second piston 20 is increased; in the process of discharging the air at the outer side and the inner side of the above-mentioned second piston 20, it can be ensured that the above-mentioned filling and air discharging are successfully performed at the same time; and after the above-mentioned filling is completed, the serum inside the subpackage bottles 13 is finely adjusted under the action of the first spring 21 so that the subpackage amounts of serum inside all the subpackage bottles 13 are kept identical; and then, the first connection hose 16, a second connection hose 27 and third connection hoses 28 are subjected to heat sealing by a heat sealing machine to disassemble the subpackage bottles 13.

In the descriptions of the present disclosure, it needs to be noted that the terms "mounted", "connected" and "connection" should be understood in a broad sense unless otherwise specified and defined, for example, "connection" may be fixed connection or detachable connection or integrated connection, may be mechanical connection or electrical connection, may be direct connection or indirect connection through an intermediate medium, and may be internal connection of two elements. For those of ordinary skill in the art, the specific meanings of the above terms in the present disclosure may be understood according to specific situations.

The above-mentioned embodiments are merely used to describe the technical solutions of the present disclosure, rather than to limit the technical solutions. Although the present disclosure has been described in detail with reference to the above-mentioned embodiments, it should be understood by those of ordinary skill in the art that the technical solutions recorded in all the above-mentioned embodiments may still be modified, or parts of the technical features may be equivalently replaced; and these modifications or replacements do not make the essences of the corresponding technical solutions depart from the scope of the technical solutions in all the embodiments of the present disclosure.

What is claimed is:

1. A sterile preparation, subpackage and output system for serum, wherein the system comprises:
    a blood collection and separation unit, configured to collect venous blood and capable of achieving centrifugal separation of the blood;
    a serum collection unit cooperating with the blood collection and separation unit and configured to achieve sterile collection of serum;
    a liquid subpackage unit cooperating with the serum collection unit and configured to achieve precise sterile subpackage of the serum; and
    a liquid boosting pen configured to achieve precise quantitative output of the serum;
    wherein an inner cavity of a container main body is provided with a first piston matched with the inner cavity,
    wherein a front end of a bottle body is provided with a bottle cap, a rear cover is screwed to a tail end of the bottle body, a second piston is disposed inside the bottle body, and a first spring is disposed between the second piston and the rear cover;
    a gland is screwed to the outer side of the rear cover, the rear cover and the gland are each provided with a hole, and a filtration membrane is disposed between the rear cover and the gland;
    a venous blood collection opening in a bottom of the container main body is provided with a first Luer taper,
    the subpackage bottle located on the tail end is provided with a first connection hose with a 0.2 m-pore-size bacteriostatic filter,
    the bottle cap of the subpackage bottle located on the front end is connected to the second Luer taper by a second connection hose;
    in two adjacent subpackage bottles, a connecting end of a front subpackage bottle is connected to the bottle cap of a rear subpackage bottle by a third connection hose; and
    the connecting end of the subpackage bottle located on the tail end is provided with the first connection hose with the 0.2 m-pore-size bacteriostatic filter.

2. The sterile preparation, subpackage and output system for serum according to claim 1, wherein the blood collection and separation unit comprises container main body,
    a detachable push rod is disposed on the outer side of the first piston, and the first Luer taper is provided with a blood collection needle or an end cap matched with the first Luer taper; and
    a skirt part on the top end of the first piston is provided with a notch, and the tail end of the push rod is matched with the notch.

3. The sterile preparation, subpackage and output system for serum according to claim 1, wherein the serum collection unit comprises a syringe (9) and a needle seat (11) for supporting an injection needle (10), wherein the front end of the syringe (9) is connected to the injection needle (10) by a medical tee (12);

the needle seat (11) is of an inverted funnel-shaped cavity structure of which the upper and lower bottom surfaces communicate; and a third end of the medical tee (12) is connected to the liquid subpackage unit.

4. The sterile preparation, subpackage and output system for serum according to claim 1, wherein the liquid subpackage unit comprises several subpackage bottles that are connected in series;

the subpackage bottle located on the front end is connected to the third end of the medical tee by a second Luer taper.

5. The sterile preparation, subpackage and output system for serum according to claim 4, wherein the subpackage bottle (13) comprises a bottle body (17), wherein the front end of the bottle body (17) is provided with a bottle cap (18), a rear cover (19) is screwed to the tail end of the bottle body (17), a second piston (20) is disposed inside the bottle body (17), and a first spring (21) is disposed between the second piston (20) and the rear cover (19); a gland (22) is screwed to the outer side of the rear cover (19), the rear cover (19) and the gland (22) are each provided with a hole (23), and a filtration membrane (24) is disposed between the rear cover (19) and the gland (22).

6. The sterile preparation, subpackage and output system for serum according to claim 5, wherein graduation lines (25) are disposed between the front end and the tail end of the bottle body (17), and the part, corresponding to the tail ends of the graduation lines (25), of the bottle body (17) is provided with a connecting end (26);

the bottle cap (18) of the subpackage bottle (13) located on the front end is connected to the second Luer taper (14) by a second connection hose (27);

in two adjacent subpackage bottles (13), the connecting end (26) of the front subpackage bottle (13) is connected to the bottle cap (18) of the rear subpackage bottle (13) by a third connection hose (28); and the connecting end (26) of the subpackage bottle (13) located on the tail end is provided with the first connection hose (16) with the 0.2 μm-pore-size bacteriostatic filter (15).

7. The sterile preparation, subpackage and output system for serum according to claim 1, wherein the liquid boosting pen comprises a pen cap (29) and a pen body supporting tube (30) screwed to the tail end of the pen cap (29), and an adjustable rear cover (31) is screwed to the tail end of the pen body supporting tube (30);

the bottle body (17) of the subpackage bottle (13) and the second piston (20) disposed inside the bottle body (17) are disposed inside the pen cap (29) and the pen body supporting tube (30), the second piston (20) is connected to a push rod (33) disposed inside a ratchet tube (32), continuous ratchet teeth (34) are disposed on the outer circumferential surface of the ratchet tube (32), a push rod positioning frame (35) and a boosting frame (36) are disposed inside the pen body supporting tube (30), the top of the boosting frame (36) is connected to a button (37), a second spring (38) is disposed between the button (37) and the pen body supporting tube (30), and the top end of the button (37) penetrates through the adjustable rear cover (31);

the push rod positioning frame (35) comprises a first mounting rack (39) that is snap-fitted in the pen body supporting tube (30), and positioning push rods (40) disposed on the bottom of the first mounting rack (39) and matched with the continuous ratchet teeth (34);

the boosting frame (36) is disposed on the inner side of the push rod positioning frame (35) and comprises boosting push rods (41) matched with the continuous ratchet teeth (34), and a second mounting rack (42) is disposed on the tops of the boosting push rods (41); and the front end of the bottle body (17) penetrates through the top of the pen cap (29).

8. The sterile preparation, subpackage and output system for serum according to claim 7, wherein the continuous ratchet teeth (34) are disposed on the two corresponding sides of the outer circumferential surface of the ratchet tube (32), the push rod positioning frame (35) comprises the two positioning push rods (40) respectively matched with the continuous ratchet teeth (34) located on the two sides, and the boosting frame (36) comprises the two boosting push rods (41) respectively matched with the continuous ratchet teeth (34) located on the two sides;

a groove (43) is disposed at the bottom end of the button (37), and the second mounting rack (42) is snap-fitted in the groove (43); and a ratchet tube notch (44) is disposed on one side of the lower parts of the continuous ratchet teeth (34).

9. A method for the sterile preparation, subpackage and output system for serum according to claim 1, wherein the method comprises the following steps:

step 1: connecting a push rod (3) to a first piston (2), enabling a blood collection needle (5) to be fixedly connected to a first Luer taper (4), and after the connection is completed, collecting venous blood;

step 2: after the collection of the venous blood is completed, dismounting the blood collection needle (5) from the first Luer taper (4), and mounting an end cap (6); and dismounting the push rod (3) from the first piston (2);

step 3: after the push rod (3) and the blood collection needle (5) are dismounted and the end cap (6) is mounted, incubating and centrifuging whole blood in a container main body (1), and layering centrifuged erythrocytes and serum, wherein the serum is a supernate;

step 4: placing a needle seat (11) which is of an inverted funnel-shaped cavity structure at the outer side of the first piston (2), and enabling an injection needle (10) to penetrate through the upper bottom surface of the needle seat (11), the lower bottom surface of the needle seat (11) and the first piston (2) to enter the serum serving as the supernate;

step 5: adjusting a medical tee (12) to enable a cavity of a syringe (9) to communicate with the container main body (1), and pressing a barrel of the syringe (9) to enable the serum serving as the supernate to enter the cavity of the syringe (9) via the container main body (1), the injection needle (10) and the medical tee (12);

step 6: adjusting the medical tee (12) to enable the cavity of the syringe (9) to communicate with a liquid subpackage unit, and boosting a pull rod of the syringe (9) to enable the serum inside the cavity of the syringe (9) to enter the liquid subpackage unit via the medical tee (12);

step 7: after enabling the serum inside the cavity of the syringe (9) to enter the liquid subpackage unit in step 6 is completed, completing subpackage; and after the subpackage is completed, disassembling the liquid subpackage unit into several subpackage bottles (13), and performing storage in a low-temperature or freezing manner;

step 8: when the serum needs to be used, enabling positioning push rods (40) and boosting push rods (41) to be matched with ratchet teeth located on the same position on a ratchet tube (32); putting a bottle body (17) into a pen cap (29), and connecting a push rod (33) inside the ratchet tube (32) to a second piston (20) in the bottle body (17); and meanwhile, screwing the pen cap (29) to a pen body supporting tube (30), mounting a second spring (38) and a button (37), and finally, screwing an adjustable rear cover (31) to the pen body supporting tube (30);

step 9: placing the bottle body (17) on the top of the pen cap (29) above a position where the serum needs to be dripped, manually pressing the button (37), driving, by the button (37), a boosting frame (36) to move towards the pen cap (29) end, pushing, by the top ends of the boosting push rods (41), the ratchet tube (32) to advance via the ratchet teeth, and pushing, by the push rod (33) in the ratchet tube (32), the second piston (20) to move towards the front end of the bottle body (17) to quantitatively output the serum;

step 10: when the above-mentioned boosting push rods (41) push the ratchet tube (32) to advance, keeping the positions of the positioning push rods (40) unchanged, and enabling the top ends of the positioning push rods (40) to enter the next ratchet teeth of continuous ratchet teeth (34); after the quantitative output of the serum is completed, releasing the button (37) to enable the button (37) to be restored under the action of the second spring (38), keeping the positions of the positioning push rods (40) for fixing the ratchet tube (32) unchanged in a restoring process, and enabling the boosting push rods (41) to be restored under the driving of the button (37) and enter the same ratchet teeth which the top ends of the positioning push rods (40) enter, thus completing the overall process of quantitative output of the serum;

step 11: after the serum in one subpackage bottle (13) is used up, replacing the subpackage bottle (13) with a new subpackage bottle (13), wherein top ends of the positioning push rods (40) and the boosting push rods (41) can enter the continuous ratchet teeth (34) via a ratchet tube notch (44) during replacement; and step 12: disposing an external thread on the outer circumferential surface of the tail end of the pen body supporting tube (30), connecting the external thread on the tail end of the pen body supporting tube (30) to an internal thread of the adjustable rear cover (31), and adjusting the stroke of the second spring (38) by adjusting the distance between the pen body supporting tube (30) and the adjustable rear cover (31); wherein the shorter the stroke of the second spring (38), the smaller the amount of the serum output every time, and the longer the stroke of the second spring (38), the greater the amount of the serum output every time.

10. The method for the sterile preparation, subpackage and output system for serum according to claim 9, wherein the specific process of enabling the serum inside the cavity of the syringe (9) to enter the liquid subpackage unit via the medical tee (12) in the step 6 is that: the pull rod of the syringe (9) is boosted to enable the serum inside the syringe (9) to enter the subpackage bottle (13) located on the front end, the pressure inside the subpackage bottle (13) is increased, the second piston (20) is pushed to move towards a gland (22) side while the pressure is increased, and when the second piston (20) moves to a first spring (21), a connecting end (26) is opened; after the connecting end (26) is opened, the serum inside the syringe (9) continuously enters the subpackage bottle (13) located on the front end, the second piston (20) causes the connecting end (26) to be completely opened under the pressure of the serum and the serum enters the next subpackage bottle (13); and after filling of all the serum inside the syringe (9) is completed, the subpackage process is ended;

in the above-mentioned filling process, the air at the outer side of the second piston (20) in each of the subpackage bottles (13) is discharged via a hole (23) in a rear cover (19), a filtration membrane (24) and a hole (23) in the gland (22) while the pressure at the front end of the second piston (20) is increased;

meanwhile, in the above-mentioned filling process, the air at the inner side of the second piston (20) enters the subpackage bottle (13) located at the tail end via the subpackage bottle (13) located at the front end and the subpackage bottles (13) located in the middle and is discharged via a first connection hose (16) with a 0.2 µm-pore-size bacteriostatic filter (15) while the pressure at the front end of the second piston (20) is increased;

in the above-mentioned process of discharging the air at the outer side and the inner side of the second piston (20), it can be ensured that the above-mentioned filling and air discharging are successfully performed at the same time; and after the above-mentioned filling is completed, the serum inside the subpackage bottles (13) is finely adjusted under the action of the first spring (21) so that the subpackage amounts of serum inside all the subpackage bottles (13) are kept identical; and then, the first connection hose (16), a second connection hose (27) and third connection hoses (28) are subjected to heat sealing by a heat sealing machine to disassemble the subpackage bottles (13).

11. The sterile preparation, subpackage and output system for serum according to claim 3, wherein the liquid subpackage unit comprises several subpackage bottles (13) that are connected in series; the subpackage bottle (13) located on the front end is connected to the third end of the medical tee (12) by a second Luer taper (14), and the subpackage bottle (13) located on the tail end is provided with a first connection hose (16) with a 0.2 µm-pore-size bacteriostatic filter (15).

12. The sterile preparation, subpackage and output system for serum according to claim 1, wherein, graduation lines are disposed between the front end and the tail end of the bottle body, and the part, corresponding to the tail ends of the graduation lines, of the bottle body is provided with a connecting end.

* * * * *